US008119356B2

(12) United States Patent
Ko et al.

(10) Patent No.: US 8,119,356 B2
(45) Date of Patent: Feb. 21, 2012

(54) IDENTIFICATION METHOD OF GLYCOPROTEINS USING A SPECIFIC LECTIN PRECIPITATION

(75) Inventors: Jeong-Heon Ko, Daejeon (KR); Yong-Sam Kim, Daejeon (KR); Hyang-Sook Yoo, Daejeon (KR); Jong-Shin Yoo, Seoul (KR); Se-Jeong Oh, Seoul (KR); Cheorl-Ho Kim, Daegu (KR); Ok-Lye Son, Ulsan (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 28 days.

(21) Appl. No.: 12/757,004

(22) Filed: Apr. 8, 2010

(65) Prior Publication Data

US 2010/0255500 A1 Oct. 7, 2010

Related U.S. Application Data

(63) Continuation of application No. PCT/KR2007/006124, filed on Nov. 30, 2007.

(30) Foreign Application Priority Data

Oct. 8, 2007 (KR) .................. 10-2007-0100916

(51) Int. Cl.
G01N 33/53 (2006.01)
(52) U.S. Cl. .............................. 435/7.1; 436/518
(58) Field of Classification Search .................. None
See application file for complete search history.

(56) References Cited

U.S. PATENT DOCUMENTS 5,427,914 A 6/1995 Dennis

FOREIGN PATENT DOCUMENTS

| JP | 61-292062 A | 12/1986 |
| JP | 63-315953 A | 12/1988 |
| KR | 10-0475642 B1 | 3/2005 |
| KR | 10-2007-0053853 | 5/2007 |

OTHER PUBLICATIONS

Ihara et al. (J. Biol. Chem. 2002 vol. 277, p. 16960-16967).*
Watanabe et al. (glycobiology 2006 vol. 16, p. 431-439).*
Hakomori et al., "Glycosphingolipids as tumor-associated and differentiation markers," Journal of the National Cancer Institute, Aug. 1983, vol. 71, No. 2, pp. 231-251.
Feizi, "Demonstration by monoclonal antibodies that carbohydrate structures of glycoproteins and glycolipids are onco-developmental antigens," Nature, Mar. 1985, vol. 314, pp. 53-57.
Miyoshi et al., "The α1-6-fucosyltransferase gene and its biological significance," Biochimica Biophysica Acta, 1999, vol. 1473, pp. 9-20.
Miyoshi et al., Overexpression of α1-6 fucosyltransferase in hepatoma cells suppresses intrahepatic metastasis after splenic injection in athymic mice, Cancer Research, May 1, 1999, vol. 59, pp. 2237-2243.
Dennis et al., "β2 1-6 branching of Asn-linked oligosaccharides is directly associated with metastasis," Science, 1987, vol. 236, pp. 582-585.
Granovsky et al., "Suppression of tumor growth and metastasis in Mgat5-deficient mice," Nature Medicine, Mar. 2000, vol. 6, No. 3, pp. 306-312.
Gu et al., "Purification and characterization of UDP-N-Acetylglucosamine: α-6-D-Mannoside β1-6N-Acetylglucosaminyltransferase (N-Acetylglucosaminyltransferase V) from a human lung cancer cell line," Journal of Biochemistry, 1993, vol. 113, pp. 614-619.
Shoreibah et al., "Isolation, characterization, and expression of a cDNA encoding N-Acetylglucosaminyltransferase V," The Journal of Biological Chemistry, Jul. 25, 1993, vol. 268, No. 21, pp. 15381-15385.
Kang et al., "Transcriptional regulation of the N-Acetylglucosaminyltransferase V gene in human bile duct carcinoma cells (HuCC-T1) is mediated by Ets-1," The Journal of Biological Chemistry, Oct. 25, 1996, vol. 271, No. 43, pp. 26706-26712.
Ko et al., "Regulation of the GnT-V promoter by transcription factor Ets-1 in various cancer cell lines," The Journal of Biological Chemistry, Aug. 13, 1999, vol. 274, No. 33, pp. 22941-22948.
Kim et al., "Identification of target proteins of N-acetylglucosaminyltransferase V and fucosyltransferase 8 in human gastric tissues by glycomic approach," Proteomics, 2004, vol. 4, pp. 3353-3358.
Kim et al., "Identification of target proteins of N-acetylglucosaminyltransferase V in human colon cancer and implications of protein tyrosine phosphatase kappa in enhanced cancer cell migration," Proteomics, 2006, vol. 6, pp. 1187-1191.
Anderson et al., "Mass spectrometric quantitation of peptides and proteins using stable isotope standards and capture by anti-peptide antibodies (SISCAPA)," Journal of Proteome Research, 2004, vol. 3, 235-244.
Egeblad et al., "New functions for the matrix metalloproteinases in cancer progression," Nature Reviews, 2002, vol. 2, pp. 161-174.
Kannagi et al., "Carbohydrate-mediated cell adhesion in cancer metastasis and angiogenesis," Cancer Sci., May 2004, vol. 95, No. 5, pp. 377-384.
International Search Report dated Jul. 8, 2008, for Application No. PCT/KR2007/006124.
Xu et al., "Comparative glycoproteomics based on lectins affinity capture of N-linked glycoproteins from human Chang liver cells and MHCC97-H cells," Proteomics 2007, vol. 7, pp. 2358-2370.
Drake et al., "Lectin capture for strategies combined with mass spectrometry for the discovery of serum glycoprotein biomarkers," Molecular & Cellular Proteomics, vol. 5. Oct. 2006, pp. 1957-1967.
Elezkurtaj et al., "Adenovirus-mediated overexpression of tissue inhibitor of metalloproteinases-1 in the liver: efficient protection against T-cell lymphoma and colon carcinoma metastasis," The Journal of Gene Medicine, 2004, vol. 6, pp. 1228-1237.

(Continued)

Primary Examiner — Jacob Cheu
(74) Attorney, Agent, or Firm — Knobbe Martens Olson & Bear LLP

(57) ABSTRACT

The present invention relates to an analyzing method of measuring the changes of glycosylation in various glycoproteins which participate in tumorigenesis and metastasis.

15 Claims, 18 Drawing Sheets

OTHER PUBLICATIONS

Holten-Andersen et al., "Plasma TIMP-1 in patients with colorectal adenomas: a prospective study," European Journal of Cancer, 2004, vol. 40, pp. 2159-2164.

Holten-Andersen et al., "Total levels of tissue inhibitor of metalloproteinases 1 in plasma yield high diagnostic sensitivity and specificity in patients with colon cancer," Clinical Cancer Research, Jan. 2002, vol. 8, pp. 156-164.

Guo et al., "Relationship between metastasis-associated phenotypes and N-glycan structure of surface glycoproteins in human hepatocarcinoma cells," Journal of Cancer Research and Clinical Oncology, 2001, vol. 127, pp. 231-236.

Yamamoto et al., $\alpha$1,6-N-Acetylglucosamine-bearing N-Glycans in human gliomas: implications for a role in regulating invasivity, Cancer Research, Jan. 1, 2000, vol. 60, pp. 134-142.

* cited by examiner

[Figure 1]
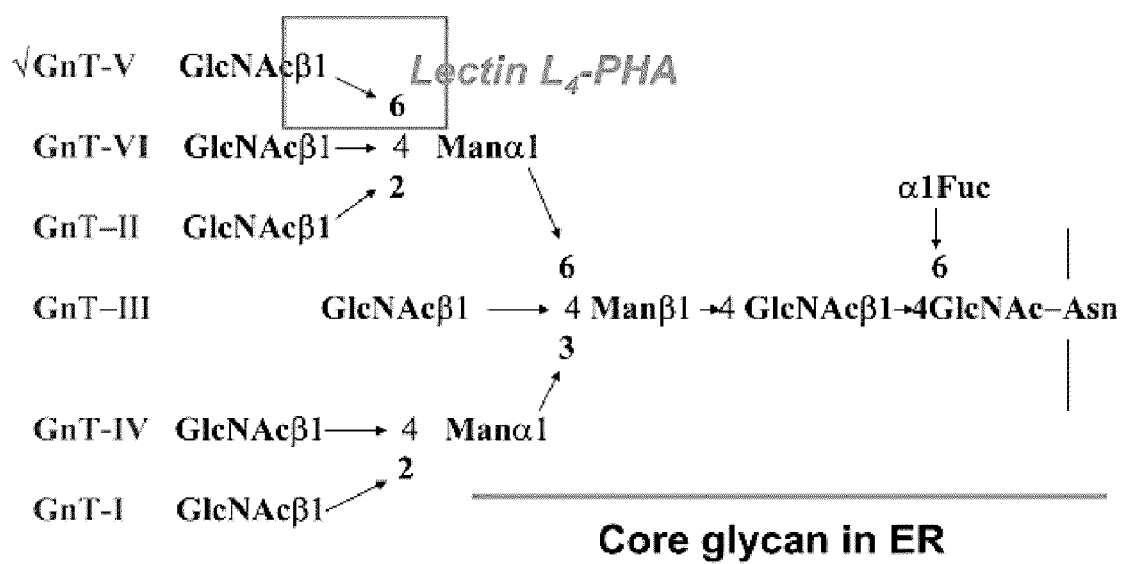

[Figure 2]
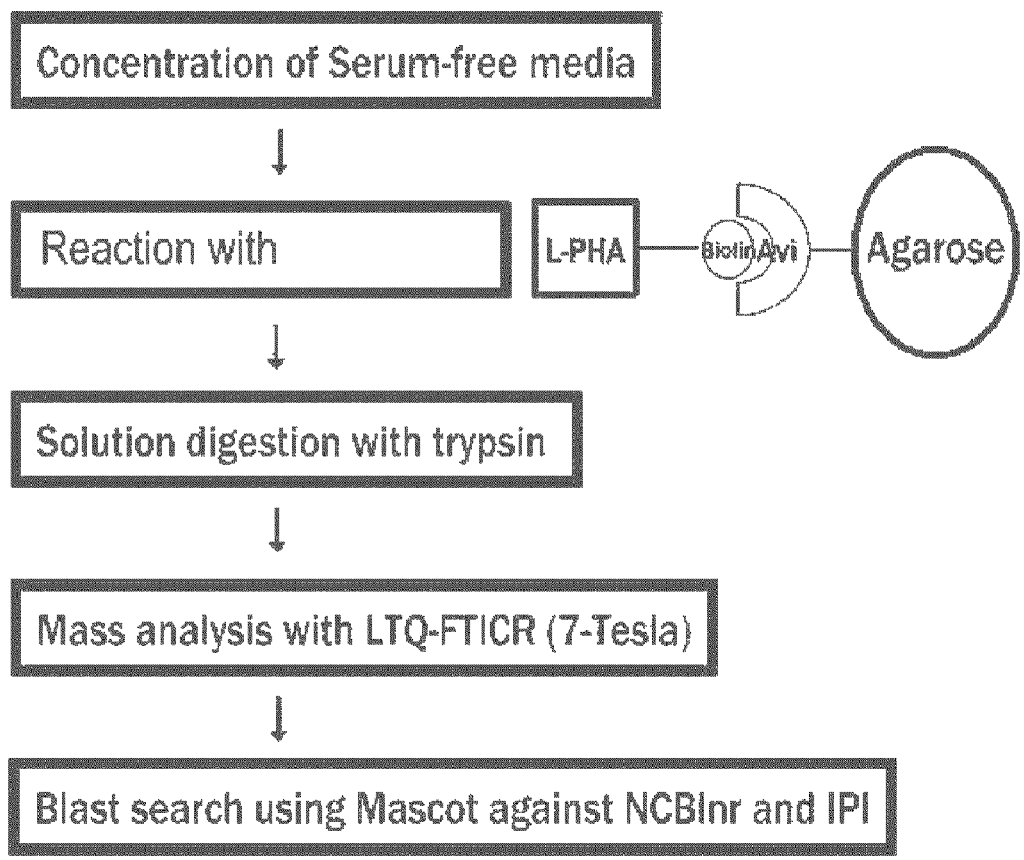

[Figure 3]

Mascot Search Results

User         : Lee juyeon
Email        : jylee@kbsi.re.kr
Search title : IPI human
MS data file : D:\Leejuyeon\support 2007\2007_pk1\0706\070614_KRIBB_KYS_FTICR\0614_KRIBB_KYS_FTICR\0614_KRIBB_KJH_V.xml
Database     : IPI_human_human_20070305 (57846 sequences; 26015783 residues)
Timestamp    : 15 Jun 2007 at 00:52:41 GMT Significant hits:
IPI00003935  Tax_Id=9606 Histone H2B type 2-E
IPI00783665  Tax_Id=9606 Laminin alpha-5 chain precursor
IPI00023845  Tax_Id=9606 Kallikrein-6 precursor
IPI00026272  Tax_Id=9606 Histone H2A type 1-B
IPI00306543  Tax_Id=9606 Growth/differentiation factor 15 precursor
IPI00024284  Tax_Id=9606 Basement membrane-specific heparan sulfate proteoglycan core protein precursor
IPI00023673  Tax_Id=9606 Galectin-3-binding protein precursor
IPI00453473  Tax_Id=9606 Histone H4
IPI00465363  Tax_Id=9606 Histone H2B type 1-A
IPI00012501  Tax_Id=9606 Isoform 1 of Regenerating islet-derived protein 4 precursor
IPI00746213  Tax_Id=9606 7 kDa protein
IPI00015785  Tax_Id=9606 Isoform 2 of Crumbs homolog 1 precursor
IPI00297188  Tax_Id=9606 Brain-specific angiogenesis inhibitor 2 precursor
IPI00787921  Tax_Id=9606 PREDICTED: SET domain containing 1B
IPI00759637  Tax_Id=9606 Isoform 4 of Titin
IPI00032293  Tax_Id=9606 Cystatin C precursor

[Figure 3] - Continued

| ID | Description |
|---|---|
| IPI00643897 | Tax_Id=9606 71 kDa protein |
| IPI00023283 | Tax_Id=9606 Isoform 2 of Titin |
| IPI00745683 | Tax_Id=9606 2549 kDa protein |
| IPI00759542 | Tax_Id=9606 Isoform 8 of Titin |
| IPI00739781 | Tax_Id=9606 PREDICTED: similar to Temporarily Assigned Gene name family member |
| IPI00643047 | Tax_Id=9606 Notch homolog 4 |
| IPI00158157 | Tax_Id=9606 nuclear transcription factor, X-box binding 1 isoform 2 |
| IPI00644163 | Tax_Id=9606 OTTHUMP00000017873 |
| IPI00375498 | Tax_Id=9606 titin isoform novex-1 |
| IPI00098412 | Tax_Id=9606 Isoform 1 of Neurogenic locus notch homolog protein 4 precursor |
| IPI00004656 | Tax_Id=9606 Beta-2-microglobulin precursor |
| IPI00296434 | Tax_Id=9606 Isoform 1 of Slit homolog 1 protein precursor |
| IPI00787623 | Tax_Id=9606 PREDICTED: similar to H2A histone family, member V isoform 2 |
| IPI00784201 | Tax_Id=9606 Centrosomal protein Cep290 |
| IPI00218094 | Tax_Id=9606 PREDICTED: hypothetical protein LOC57714 |
| IPI00055784 | Tax_Id=9606 Keratin-associated protein 5-2 |
| IPI00289776 | Tax_Id=9606 Isoform 1 of Probable ubiquitin ligase protein MYCBP2 |
| IPI00029819 | Tax_Id=9606 Neurogenic locus notch homolog protein 3 precursor |
| IPI00022353 | Tax_Id=9606 Non-receptor tyrosine-protein kinase TYK2 |
| IPI00418171 | Tax_Id=9606 Keratin-associated protein 5-1 |
| IPI00736019 | Tax_Id=9606 PREDICTED: similar to kelch-like 17 |
| IPI00377045 | Tax_Id=9606 laminin alpha 3 subunit isoform 1 |
| IPI00410150 | Tax_Id=9606 Isoform 1 of Usherin precursor |
| IPI00171087 | Tax_Id=9606 S1 RNA binding domain 1 |
| IPI00455316 | Tax_Id=9606 Isoform 1 of Extracellular matrix protein FRAS1 precursor |
| IPI00184266 | Tax_Id=9606 LAMB4 protein (Fragment) |

[Figure 3] - Continued

| | |
|---|---|
| IPI00377244 | Tax_Id=9606 Isoform 2 of Myeloid/lymphoid or mixed-lineage leukemia protein 2 |
| IPI00010320 | Tax_Id=9606 Chromobox protein homolog 1 |
| IPI00025564 | Tax_Id=9606 MLN protein |
| IPI00480107 | Tax_Id=9606 565 kDa protein |
| IPI00030153 | Tax_Id=9606 OTTHUMP00000016553 |
| IPI00028382 | Tax_Id=9606 Huntingtin-associated protein-interacting protein |
| IPI00218725 | Tax_Id=9606 laminin alpha 2 subunit precursor |
| IPI00023532 | Tax_Id=9606 Hypothetical protein DKFZp564A2416 |
| IPI00438355 | Tax_Id=9606 Fibrillin-3 precursor |
| IPI00045512 | Tax_Id=9606 hemicentin 1 |
| IPI00013400 | Tax_Id=9606 Matrilysin precursor |
| IPI00073196 | Tax_Id=9606 Isoform 1 of Latent-transforming growth factor beta-binding protein 3 precursor |
| IPI00742936 | Tax_Id=9606 sacsin |
| IPI00328762 | Tax_Id=9606 ATP binding cassette, sub-family A (ABC1), member 13 |
| IPI00438000 | Tax_Id=9606 Keratin-associated protein 5-6 |
| IPI00377042 | Tax_Id=9606 Isoform 2 of CUB and sushi domain-containing protein 3 precursor |
| IPI00410585 | Tax_Id=9606 Isoform 1 of Crumbs homolog 2 precursor |
| IPI00217773 | Tax_Id=9606 Zinc finger, ZZ-type containing 3 |
| IPI00739099 | Tax_Id=9606 Collagen alpha-2(V) chain precursor |
| IPI00784458 | Tax_Id=9606 312 kDa protein |

* Too many non-glycoproteins
* No TIMP-1

[Figure 4]
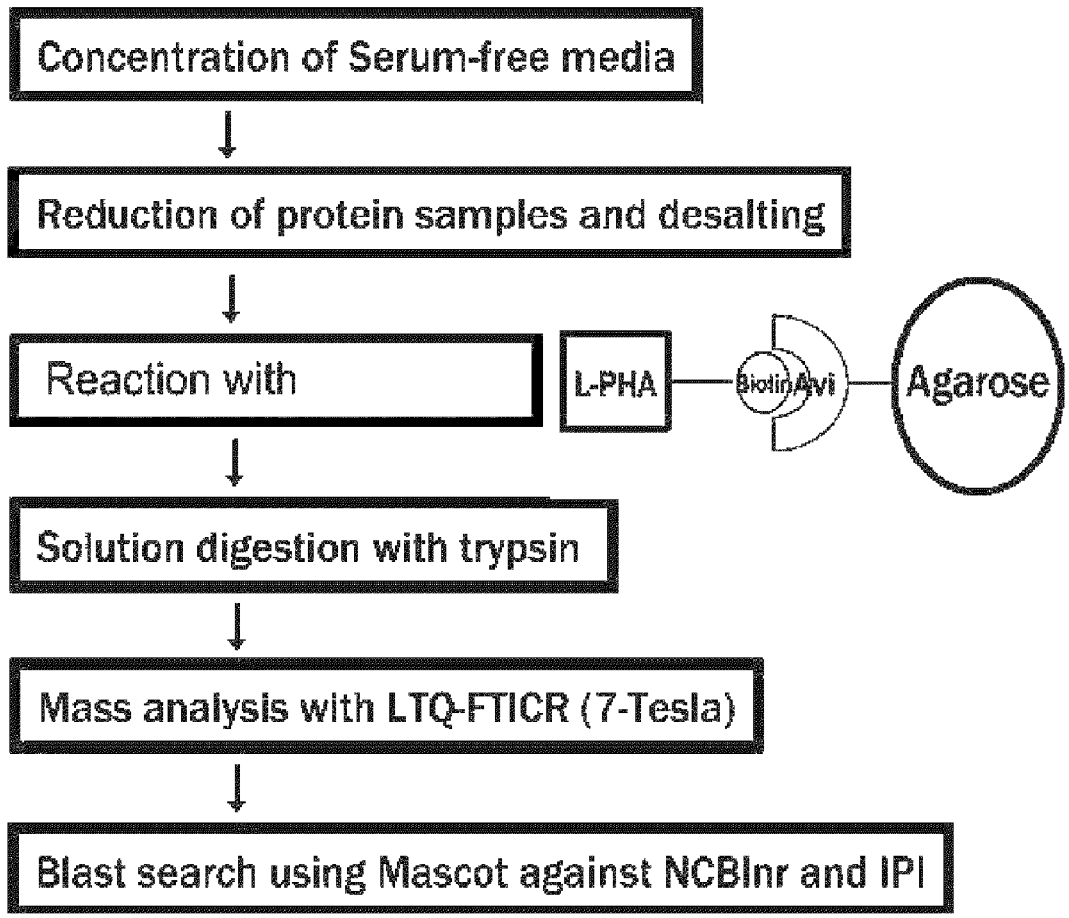

[Figure 5]

2. IPI00783665        Mass: 399452    Score: 136    Queries matched: 15
Tax_Id=9606 Laminin alpha-5 chain precursor ☐ Check to include this hit in error tolerant search or archive report

| Query | Observed | Mr(expt) | Mr(calc) | Delta | Miss | Score | Expect | Rank | Peptide |
|---|---|---|---|---|---|---|---|---|---|
| 1200 | 570.5126 | 1139.0107 | 1140.4982 | -1.4875 | 0 | 6 | 2.6e-002 | 5 | R.AHVEGPSCDR.C (SEQ ID NO:2) + Propionamide (C) |
| 1201 | 570.7656 | 1139.5166 | 1140.4982 | -0.9816 | 0 | (6) | 3e-002 | 2 | R.AHVEGPSCDR.C (SEQ ID NO:2) + Propionamide (C) |
| 1254 | 578.7977 | 1155.5808 | 1155.5825 | -0.0017 | 0 | 40 | 0.13 | 1 | R.MVQSPPLSR.G (SEQ ID NO:3) |
| 227 | 432.8875 | 1295.6406 | 1295.6404 | 0.0002 | 1 | 16 | 27 | 1 | R.YWRGAMSVSGR.V (SEQ ID NO:4) |
| 428 | 472.2748 | 1413.8026 | 1414.7106 | -0.9080 | 0 | 18 | 19 | 1 | R.DHYLPDLHHLR.L (SEQ ID NO:5) |
| 1001 | 551.9334 | 1652.7782 | 1652.7828 | -0.0045 | 0 | 29 | 1.4 | 1 | R.LELERAATPEGHAMR.F (SEQ ID NO:6) |
| 1714 | 654.5392 | 1960.5957 | 1960.0159 | 0.5798 | 1 | 3 | 4.7e-002 | 5 | K.RLNTTGVSAGCTADLLVGR.A (SEQ ID NO:7) + Carbamidomethyl (C) |
| 2267 | 753.5005 | 2257.4798 | 2256.9925 | 0.4873 | 1 | 8 | 1.4e-002 | 6 | K.CDQCSLGIFSLDAANPKGCTR.C (SEQ ID NO:8) + Propionamide (C) |
| 2540 | 826.5018 | 2476.4835 | 2477.8949 | -1.4115 | 0 | 4 | 3.8e-002 | 4 | R.CDCTPCGTEACDPHSGHCLCK.A (SEQ ID NO:9) + 4Carbamidomethyl(C);Propionamide(C) |
| 2542 | 826.5048 | 2476.4925 | 2477.8949 | -1.4025 | 0 | (3) | 4.9e-002 | 10 | R.CDCTPCGTEACDPHSGHCLCK.A (SEQ ID NO:9) + 4Carbamidomethyl(c);Propionamide(c) |
| 2694 | 883.4658 | 2647.3756 | 2646.1948 | 1.1808 | 0 | 4 | 4.1e-002 | 5 | R.EQVLPAGQITVHCDCSAAGTQGNACR.K (SEQ ID NO:10) + 2 Propionamide (C) |
| 2708 | 890.6516 | 2668.9328 | 2669.1607 | -0.2278 | 1 | 10 | 86 | 1 | R.CKPGFWGLSPSNPEGCTRCSCDLR.G (SEQ ID NO:11) + Carbamidomethyl (C) |
| 2726 | 898.1050 | 2691.2931 | 2690.2113 | 1.0788 | 0 | 6 | 2.2e-002 | 1 | R.ADDGAGEFSTSVTRPSVLCDGQWHR.L (SEQ ID NO:12) |
| 2796 | 949.1179 | 2844.3319 | 2845.3269 | -0.9949 | 1 | 10 | 91 | 1 | R.EQVLPAGQITVHCDCSAAGTQGNACRK.D (SEQ ID NO:13) + 3 Propionamide (C) |
| 3011 | 1108.9220 | 3323.7442 | 3324.4024 | -0.6583 | 0 | 2 | 5e-002 | 10 | R.GVLGGVAECQPGTGQCFCKPHVCGQACASCK.D (SEQ ID NO:14) + 5 Carbamidomethyl(c) |

16. IPI00032293       Mass: 15789     Score: 62     Queries matched: 2
Tax_Id=9606 Cystatin C precursor ☐ Check to include this hit in error tolerant search or archive report

| Query | Observed | Mr(expt) | Mr(calc) | Delta | Miss | Score | Expect | Rank | Peptide |
|---|---|---|---|---|---|---|---|---|---|
| 1503 | 613.8059 | 1225.5973 | 1225.5978 | -0.0006 | 0 | 50 | 0.011 | 1 | R.ALDFAVGEYNK.A (SEQ ID NO:15) |
| 1440 | 600.9683 | 1799.8837 | 1799.8835 | 0.0002 | 1 | 32 | 0.64 | 1 | R.LVGGENDASVEEEGVTR.A (SEQ ID NO:16) |

* Identification with too low score values
* No TIMP-1

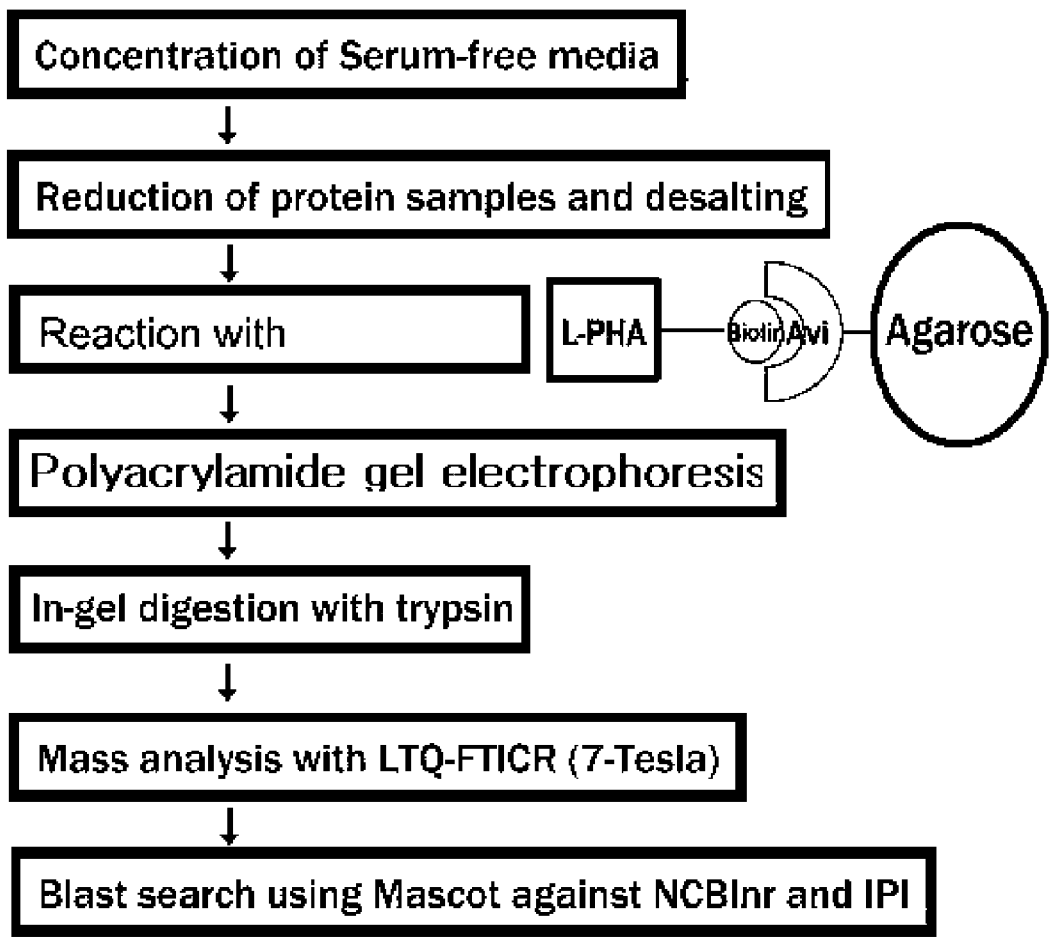
[Figure 6]

[Figure 7]

16. gi|60416883    Mass: 65389    Score: 462    Queries matched: 12

Calpectin 5 binding protein [Homo sapiens]

☐ Check to include this hit in error tolerant search or archive report

| Query | Observed | Mr(expt) | Mr(calc) | Delta | Miss | Score | Expect | Rank | Peptide |
|---|---|---|---|---|---|---|---|---|---|
| ☐ 22 | 413.7266 | 825.4386 | 825.4384 | 0.0002 | 0 | 26 | 2.3 | 1 | R.VEIFSR.G (SEQ ID NO:17) |
| ☐ 151 | 488.2900 | 974.5655 | 974.5648 | 0.0007 | 0 | 51 | 0.0091 | 1 | R.DNYLSSYR.C (SEQ ID NO:18) |
| ☐ 365 | 662.8896 | 1325.6470 | 1325.6462 | 0.0008 | 0 | 39 | 0.15 | 1 | R.ASHEVEDKIVK.I (SEQ ID NO:19) |
| ☐ 395 | 678.3991 | 1354.7716 | 1354.7707 | 0.0008 | 0 | (23) | 4.7 | 1 | R.SDLAVPSLALLK.A (SEQ ID NO:20) |
| ☐ 395 | 678.3935 | 1354.7724 | 1354.7707 | 0.0017 | 0 | 56 | 0.002 | 1 | R.SDLAVPSLALLK.A (SEQ ID NO:20) |
| ☐ 1018 | 796.9006 | 1591.7866 | 1591.7841 | 0.0024 | 0 | 68 | 0.00012 | 1 | R.ELSEALQITDSQR.G (SEQ ID NO:21) |
| ☐ 929 | 531.6035 | 1591.7887 | 1591.7841 | 0.0046 | 0 | (46) | 0.023 | 1 | R.ELSEALQITDSQR.G (SEQ ID NO:21) |
| ☐ 2812 | 1081.5199 | 2161.0172 | 2161.0116 | 0.0056 | 0 | (108) | 7.6e-009 | 1 | R.ITSPTVAFVDSVMAR.R (SEQ ID NO:22) |
| ☐ 2815 | 1082.0173 | 2162.0201 | 2161.0116 | 1.0085 | 0 | 120 | 4.7e-010 | 1 | R.ITSPTVAFVDSVMAR.R (SEQ ID NO:22) |
| ☐ 3565 | 841.3998 | 2521.1775 | 2520.1750 | 1.0025 | 0 | 29 | 0.84 | 1 | R.VPTVSNVPDPSFLQDK.R (SEQ ID NO:23) |
| ☐ 3610 | 1399.6370 | 2797.2594 | 2798.2560 | -0.9967 | 0 | 14 | 13 | 1 | R.AAFGQGSPIDLDVVQTQTEASLQVK.S (SEQ ID NO:24) |
| ☐ 3615 | 1407.6285 | 2813.2425 | 2814.2509 | -1.0084 | 0 | (11) | 20 | 1 | R.AAFGQGSPIDLDVVQTQTEASLQVK.S (SEQ ID NO:24) + Oxidation (M) |

[Figure 7] - Continued 110. gi|31189    Mass: 23184    Score: 119    Queries matched: 6
unnamed protein product [Homo sapiens]

☐ Check to include this hit in error tolerant search or archive report

| Query | Observed | Mr(expt) | Mr(calc) | Delta | Miss | Score | Expect | Rank | Peptide |
|---|---|---|---|---|---|---|---|---|---|
| ☑ 194 | 497.2670 | 992.5195 | 992.5178 | 0.0017 | 0 | 45 | 0.034 | 1 | R.SEEFLIAGK.L (SEQ ID NO:25) |
| ☑ 561 | 617.3123 | 1232.6101 | 1232.6149 | -0.0048 | 0 | (15) | 32 | 5 | K.GFQALGDAADIR.F (SEQ ID NO:26) |
| ☑ 562 | 617.3150 | 1232.6155 | 1232.6149 | 0.0006 | 0 | (61) | 0.00082 | 1 | K.GFQALGDAADIR.F (SEQ ID NO:26) |
| ☑ 563 | 617.3152 | 1232.6159 | 1232.6149 | 0.0010 | 0 | 74 | 3.4e-005 | 1 | K.GFQALGDAADIR.F (SEQ ID NO:26) |
| ☑ 564 | 617.3153 | 1232.6161 | 1232.6149 | 0.0012 | 0 | (71) | 7.5e-005 | 1 | K.GFQALGDAADIR.F (SEQ ID NO:26) |
| ☑ 565 | 617.3156 | 1232.6166 | 1232.6149 | 0.0017 | 0 | (37) | 0.2 | 1 | K.GFQALGDAADIR.F (SEQ ID NO:26) |

Proteins matching the same set of peptides:

gi|220125    Mass: 18302    Score: 119    Queries matched: 6
tissue inhibitor of metalloproteinases [Homo sapiens]

gi|4120013    Mass: 20605    Score: 119    Queries matched: 6
Chain D, Mmp-3TIMP-1 Complex gi|34811011    Mass: 14245    Score: 119    Queries matched: 6
Chain B, Orientation In Solution Of Mmp-3 Catalytic Domain And N- Timp-1 From Residual Dipolar Coup gi|157210053    Mass: 23156    Score: 119    Queries matched: 5
tissue inhibitor of metalloproteinase 1 (erythroid potentiating activity, collagenase inhibitor) [H

[Figure 8]

Confirmed Candidates

| | |
|---|---|
| IPI00029273 | Tax_Id=9606 Isoform 1 of Hepatocyte growth factor receptor precursor |
| IPI00023673 | Tax_Id=9606 Galectin-3-binding protein precursor |
| IPI00013976 | Tax_Id=9606 Laminin beta-1 chain precursor |
| IPI00298281 | Tax_Id=9606 Laminin gamma-1 chain precursor |
| IPI00024284 | Tax_Id=9606 Basement membrane-specific heparan sulfate proteoglycan core protein precursor |
| IPI00377045 | Tax_Id=9606 laminin alpha 3 subunit isoform 1 |
| IPI00027486 | Tax_Id=9606 Carcinoembryonic antigen-related cell adhesion molecule 5 precursor |
| IPI00783665 | Tax_Id=9606 Laminin alpha-5 chain precursor |
| IPI00299404 | Tax_Id=9606 Laminin beta-3 chain precursor |
| IPI00019591 | Tax_Id=9606 Isoform 1 of Complement factor B precursor (Fragment) |
| IPI00032292 | Tax_Id=9606 Metalloproteinase inhibitor 1 precursor |
| IPI00412982 | Tax_Id=9606 Neurogenic locus notch homolog protein 1 precursor |
| IPI00746807 | Tax_Id=9606 brain-specific angiogenesis inhibitor 2 |
| IPI00401776 | Tax_Id=9606 PREDICTED: similar to mucin 6, gastric isoform 1 |
| IPI00786844 | Tax_Id=9606 PREDICTED: similar to notch 2 preproprotein |
| IPI00168520 | Tax_Id=9606 Isoform 2 of Matrilin-2 precursor |
| IPI00783464 | Tax_Id=9606 dynein heavy chain domain 3 |
| IPI00007596 | Tax_Id=9606 ADAM 21 precursor |
| IPI00000151 | Tax_Id=9606 Integrin beta-6 precursor |
| IPI00418465 | Tax_Id=9606 CD44 antigen isoform 2 precursor |
| IPI00480153 | Tax_Id=9606 Receptor tyrosine kinase-like orphan receptor 2 |
| IPI00007834 | Tax_Id=9606 Isoform 1 of Ankyrin-2 |
| IPI00220096 | Tax_Id=9606 Isoform 6 of Zonadhesin precursor |

[Figure 9]

Newly Identified Candidates

IPI00292579 Tax_Id=9606 Stabilin-2 precursor
IPI00026892 Tax_Id=9606 Metallothionein-4
IPI00254408 Tax_Id=9606 fetal Alzheimer antigen isoform 1
IPI00401776 Tax_Id=9606 PREDICTED: similar to mucin 6, gastric isoform 1
IPI00073196 Tax_Id=9606 Isoform 1 of Latent-transforming growth factor beta-binding protein 3 precursor
IPI00643014 Tax_Id=9606 retinoblastoma-associated factor 600
IPI00641693 Tax_Id=9606 400 kDa protein
IPI00387168 Tax_Id=9606 Isoform 1 of Proprotein convertase subtilisin/kexin type 9 precursor
IPI00020557 Tax_Id=9606 Low-density lipoprotein receptor-related protein 1 precursor
IPI00025276 Tax_Id=9606 Isoform XB of Tenascin-X precursor
IPI00219596 Tax_Id=9606 Isoform B of ADAMTS-14 precursor
IPI00455317 Tax_Id=9606 Isoform 3 of Extracellular Matrix protein FRAS1 precursor
IPI00746753 Tax_Id=9606 Proprotein convertase subtilisin\/kexin type 5
IPI00737886 Tax_Id=9606 PREDICTED: similar to mucin 19
IPI00215722 Tax_Id=9606 Isoform JM-B of Receptor tyrosine-protein kinase erbB-4 precursor
IPI00377244 Tax_Id=9606 Isoform 2 of Myeloid/lymphoid or mixed-lineage leukemia protein 2
IPI00301360 Tax_Id=9606 Isoform 1 of Tumor protein p73-like

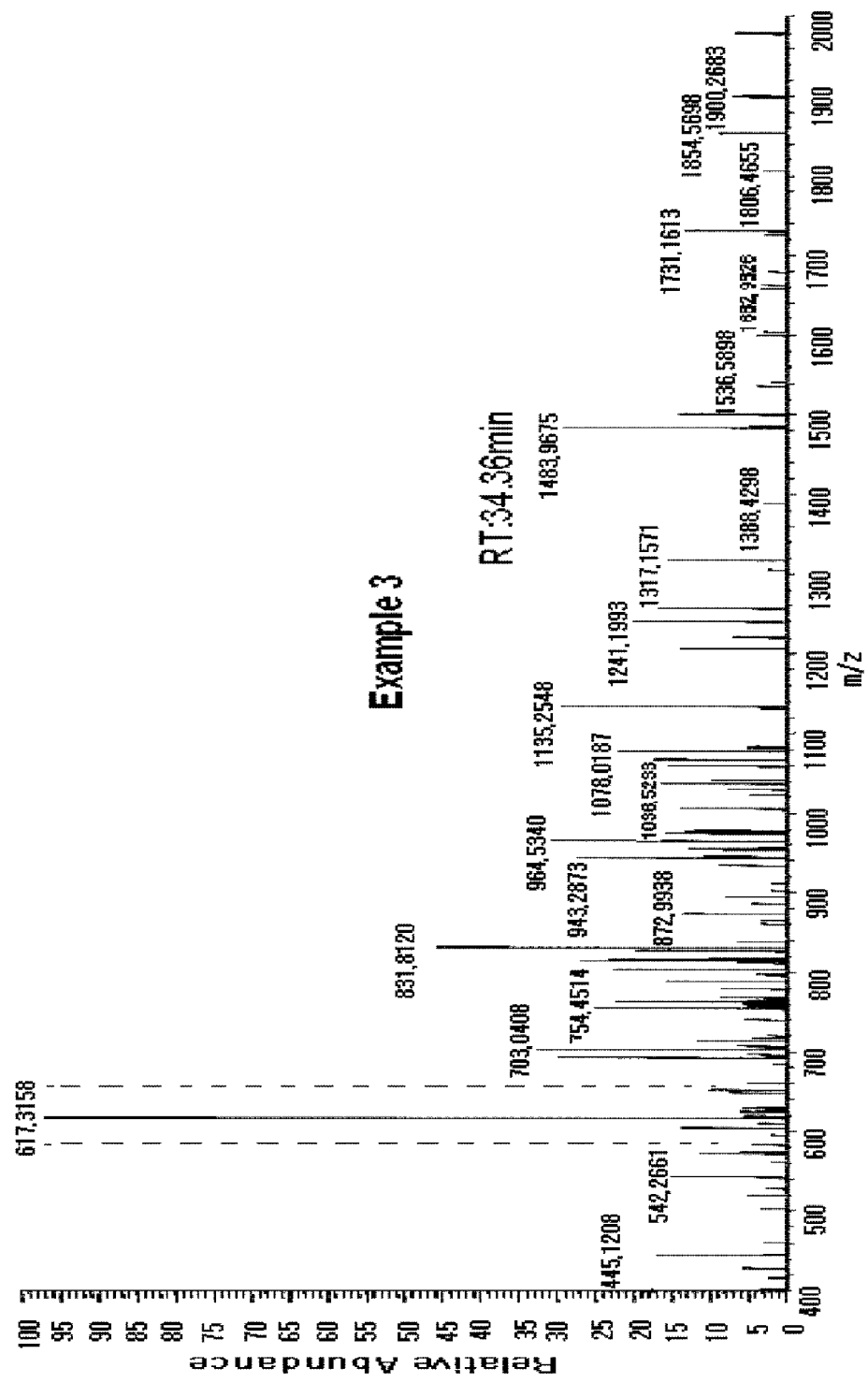
[Figure 10]

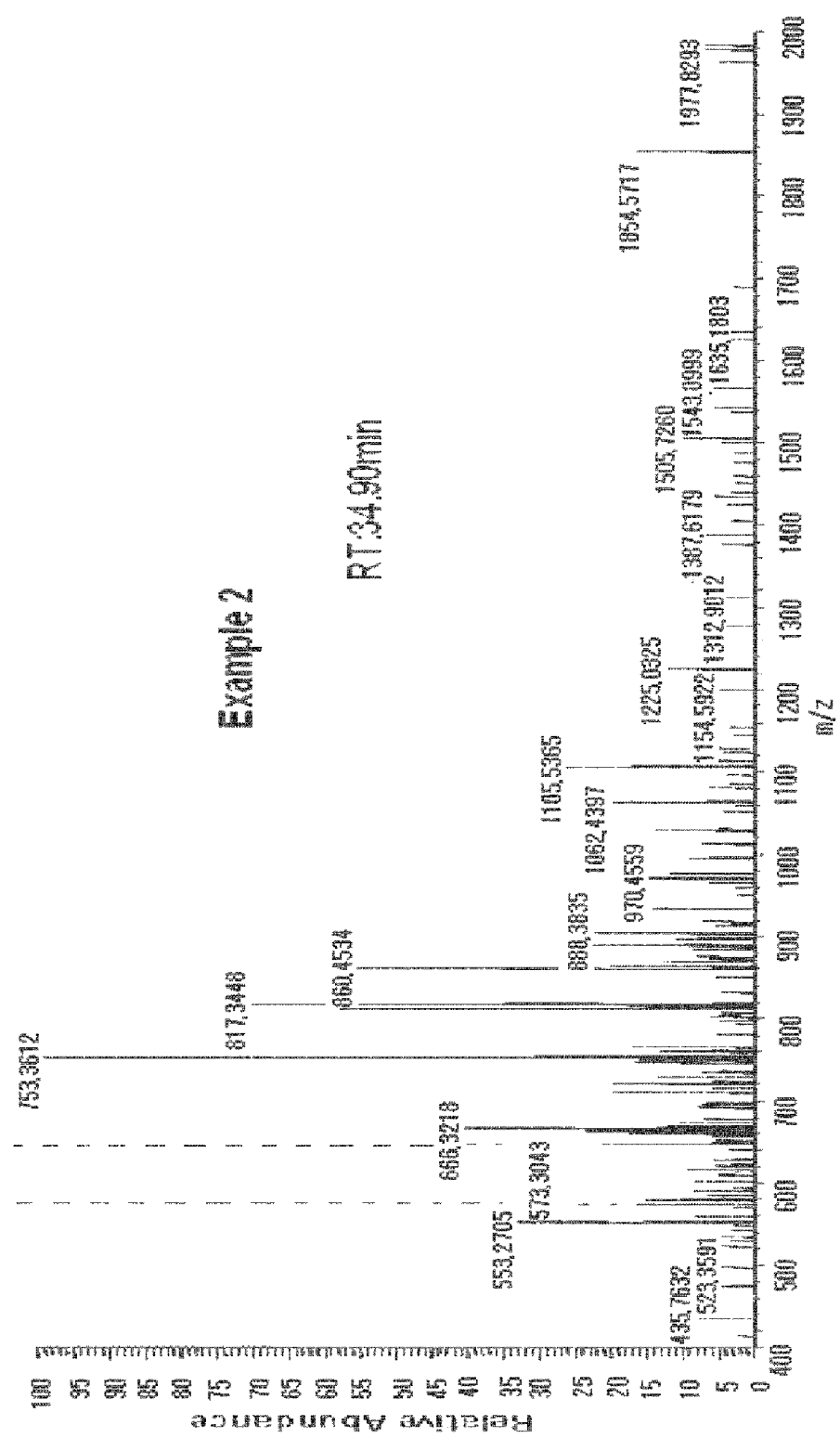
[Figure 10] - Continued

[Figure 11]
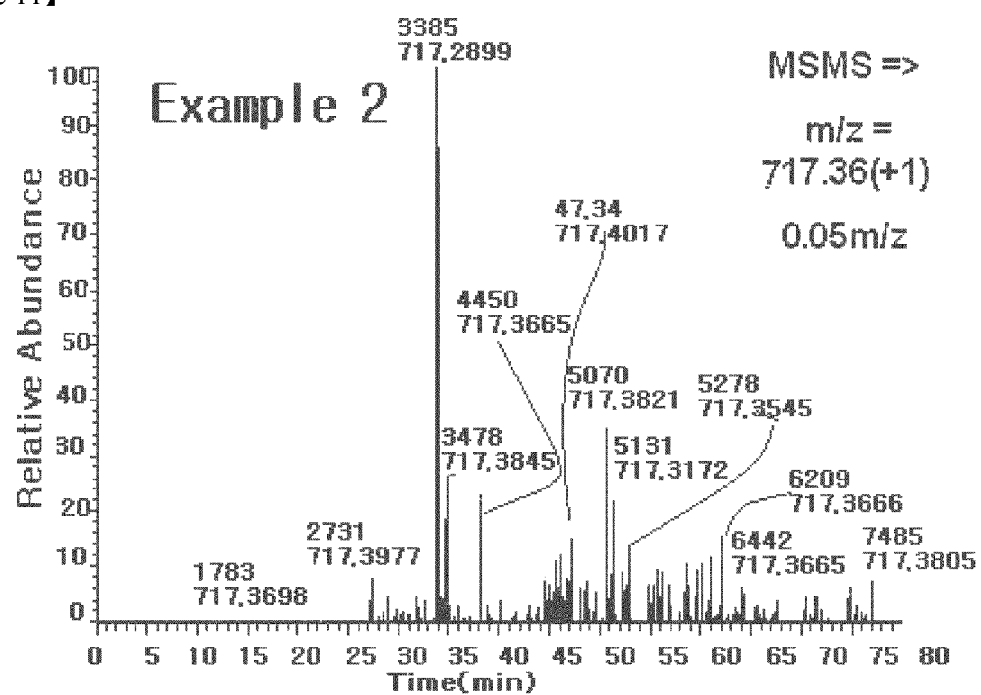

[Figure 11] -Continued
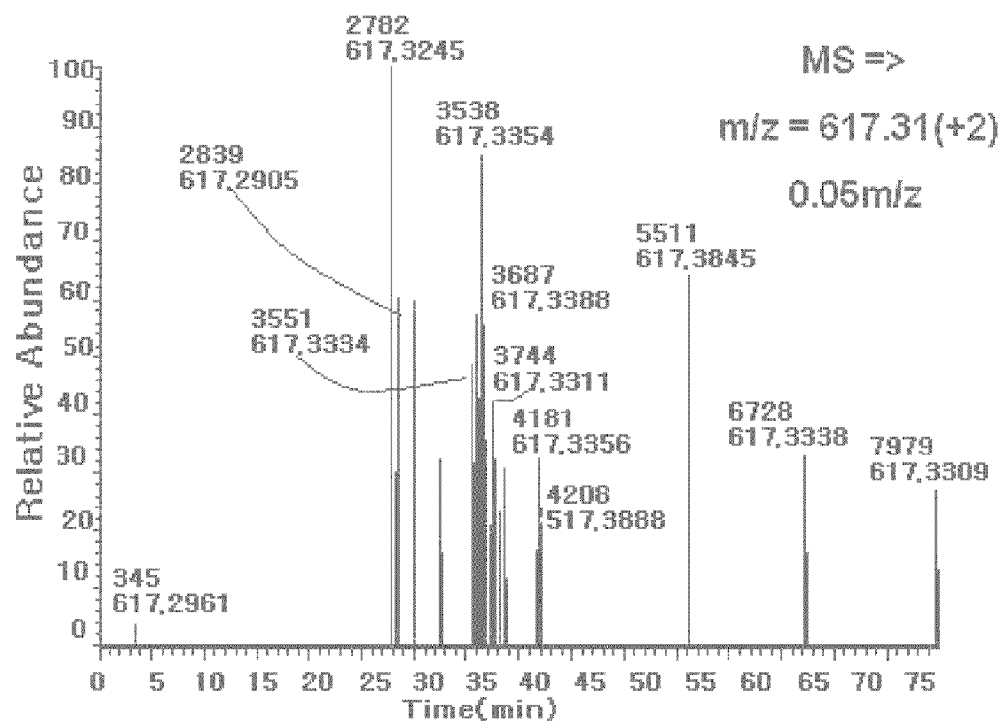

[Figure 11] -Continued
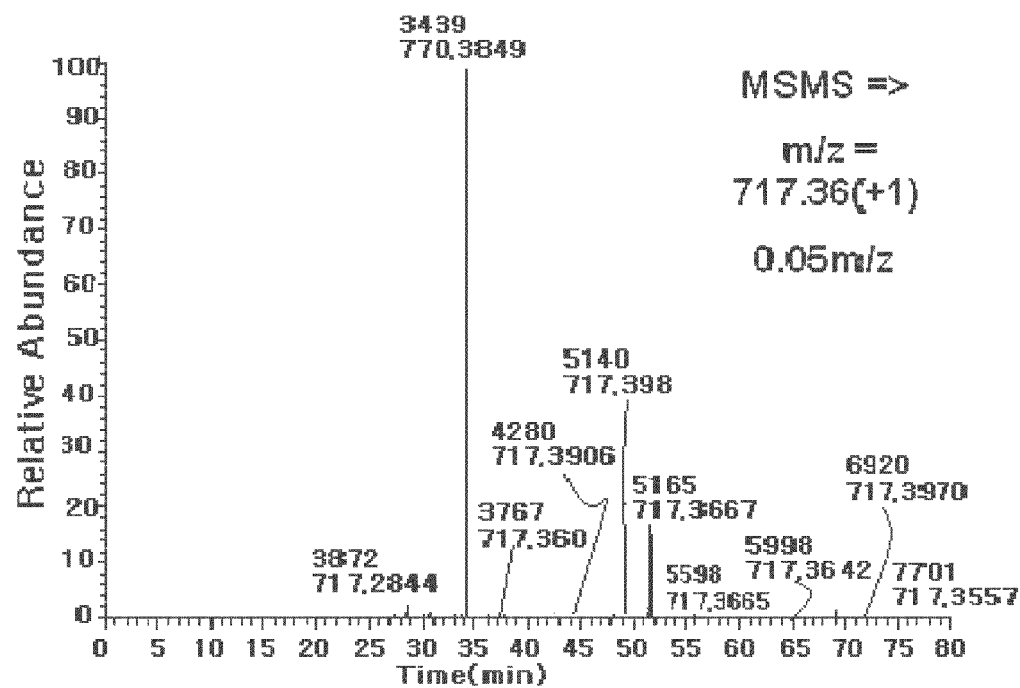

[Figure 11] -Continued
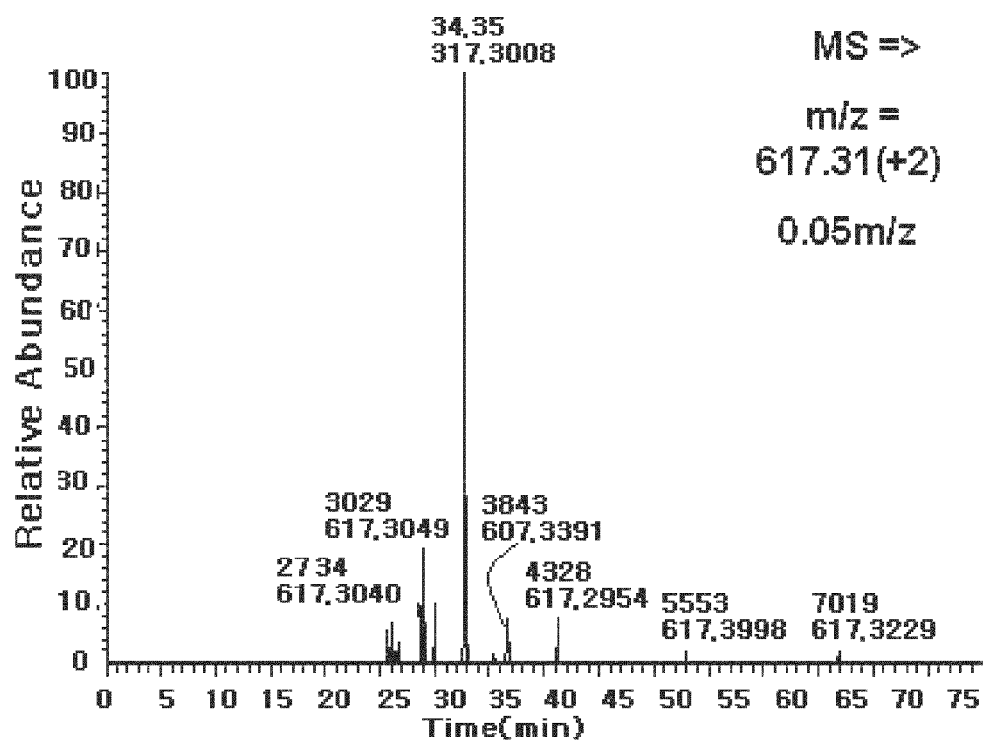

IDENTIFICATION METHOD OF GLYCOPROTEINS USING A SPECIFIC LECTIN PRECIPITATION

CROSS-REFERENCE TO RELATED PATENT APPLICATIONS

This application is a continuation application under 35 U.S.C. §365(c) of International Application No. PCT/KR2007/006124, filed Nov. 30, 2007 designating the United States. The International Application No. PCT/KR2007/006124 was published in English as WO2009/048196 A1 on Apr. 16, 2009. This application further claims the benefit of the earlier filing date under 35 U.S.C. §365(b) of Korean Patent Application No. 10-2007-0100916 filed Oct. 8, 2007. This application incorporates herein by reference the International Application No. PCT/KR2007/006124 including the International Publication No. WO2009/048196 A1 and the Korean Patent Application No. 10-2007-0100916 in their entirety.

BACKGROUND

1. Field

The present invention relates to a detection method of glycoproteins that exhibit an alteration in glycosylation in the course of tumorigenesis and cancer metastasis. More specifically, the present invention relates to a mass spectrometry (MS)-based identification of N-linked glycoproteins that are modified during cancer development and progression.

2. Discussion of the Related Technology

Two-dimensional electrophoresis allowed to identify and characterize proteins with ease and in a high-throughput manner when connected to such highly sophisticated analyzers as MALDI-TOF (Matrix Assisted Laser Desorption/Ionization Time-of-Flight) mass spectrometry and amino acid sequencers, whose developments have facilitated the 'post-genomics proteomics era'. However, the proteomics approaches have a limitation in that they present a fixed state of proteome rather than revealing a biological dynamism. In fact, signal transduction pathways in cells generally exhibits an dynamism in the expression level of proteins and post-translational modification (PTM).

Moreover, it is often difficult to monitor the proteins on the signal transduction pathway by displaying 2-D gels since the proteins exist sparsely in cells. Protein glycosylation allows to overcome these limitations and to observe cells on a dynamism-basis. Changes in proteins level that can not be discerned by simple staining are easily monitored when alterations in glycosylation are chased with a specific lectin.

Recently, this approach, termed 'glycomics', has emerged as a promising field that help overcome the limitations of the conventional proteomics. Glycomics is mainly based on pursuit of alterations in protein glycosylation, a major class of post-translational modification.

One of the biological disturbances is an aberrant glycosylation of proteins, which is induced by a signal of a certain oncogene and causes, in turn, a dysfunction of cell adhesion, cell-cell recognition and eventually tumorigenesis and cancer malignancy (Hakomori and Kannagi, 1983, J. Natl. Cancer Inst., 71:231-251; Feizi, 1985, Nature, 314:53-57). Matured mRNA is translated on an endoplasmic reticulum, where core glycan moiety of N-linked glycosylation is also generated. After that, the glycoproteins are translocated to Golgi body where supplementary glycans are attached by such glycosyltransferase as illustrated in FIG. 1. The glycosyltransferases are activated by a signal elicited by the specific oncogenes, such as ras, raf, ets, and so on. One of the glycosyltransferases that draw interests is FUT8, which catalyzes an addition of fucose to the core N-acetylglucosamine (GlcNAc) of N-glycan. Alpha-fetoprotein (AFP) and antitrypsin are widely known to exemplify the importance of a fucosylation in cancer malignancy (Miyoshi, E., Ko, J. H. et al., 1999, Biochim. Biophys. Acta 1473: 9-20). FUT8 (Fucosyl transferase 8) responsible for the fucosylation was purified and the cDNA was cloned by Taniguchi group and when FUT8-transfected Hep3B (Hep3B-FT) was injected into the spleen of athymic mice, tumor formation in the liver was dramatically suppressed in the transfectants compared to the parental cells (Miyoshi, E., Ko, J. H. et al., 1999, Cancer Research 59: 2237-2243). Lens culinaris agglutinin (LCA) bind the fucose attached to the innermost GlcNAc of N-glycan and also core N-glycan like Con A.

The aberrant glycosylation induced by N-acetylglucosaminyltransferase V (GnT-V) is a representative example of such protein modifications as are implicated in the tumor invasion and metastasis (Dennis et al., 1987, Science, 236: 582-585). Following the attachment of core glycans on endoplasmic reticulum, the supplementary glycans are decorated in Golgi body primarily by 6 types of N-acetylglucosaminyltranferase (I-VI). Of these, GnT-V is known to be associated with metastatic potential of cancer cells by modifying the target glycoproteins and changing the properties of recognition and cell adhesion of cancer cells.

GnT-V was first noticed by the report of Dennis et al. (1987) that the β1,6 branches were remarkably represented as cancer tissues were growing or during metastasis (Dennis, et al., 1987, Science, 236: 582-585). A cell surface protein gp130 is one or major target proteins of GnT-V and shows high metastasis activity when β1,6 N-acetylglucosamine is added. GnT-V knockout mice were established in which GnT-V was deficient in their embryonic stem (ES) cells and to which polyomavirus middle T antigen (reffered "PyMT" hereinafter) viral oncogene was introduced in order to induce a cancer. Resultingly, the growth of cancer and metastasis induced by PyMT were remarkably inhibited in GnT-V knockout mice comparing with another normal mice group in which only PyMT was over-expressed (Granovsky et al., 2000, Nature Med., 6: 306-312), and the growth of β1,6 branch caused high metastasis especially in mice with breast cancer. As shown above, GnT-V relates to cancer metastasis and represents high matastasis activity in various tissues. GnT-V was purified in the human lung cancer cell and the mouse kidney, the cDNA was cloned, and the promoter and genomic structure was resolved (Gu et al., 1993, J Biochem, 113:614-619; Soreibah et al., 1993, J. Biol. Chem., 268: 15381-15385; Kang et al., 1996, J. Biol. Chem., 271:26706-26712). The inventor of the present invention has reported that the transcription factor ets-1 is involved in the expression of GnT-V (Ko, et al., 1999, J. Biol. Chem., 274(33): 22941-22948). Limitations of the drug-based cancer treatment triggered a paradigm shift in the medical cancer researches toward early detection at a curable stage, and the aberrant glycoproteins are being tested for use as a cancer early-detection marker.

In accordance with this, the inventors of the present invention have reported a list of candidate proteins from cancer cells with high GnT-V overexpression that show an attachment of β1,6-GlcNAc by GnT-V using 2-dimensional electrophoresis and mass spectrometry (Kim et al., 2004, Proteomics, 4: 3353-3358; Kim et al., 2006, Proteomics, 6: 1187-1191). However, the previous gel-based resolution procedures innately have a high incidence of false-positive rates in the identification of sparse proteins. To overcome this, the inventors completed the present invention by enriching β1,6-GlcNAc-carrying glycoproteins using L-PHA lectin to identify them.

SUMMARY

One aspect of the invention provides a method of analyzing a sample to determine a level of a β1,6-N-acetylglucosamine-containing glycoprotein. The method comprises: providing a test agent comprising a first complex, wherein the first complex comprises a glycan bead and an phytohemagglutinin-L4 ($L_4$-PHA) moiety connected to the glycan bead, wherein the $L_4$-PHA moiety comprises a binding site specific to β1,6-N-acetylglucosamine; providing a sample comprising a β1,6-N-acetylglucosamine-containing glycoprotein; contacting the test agent with the sample to provide a test mixture, in which the β1,6-N-acetylglucosamine-containing glycoprotein binds with the first complex at the binding site, thereby forming a second complex in the mixture, wherein the second complex comprises the glycan bead, the $L_4$-PHA moiety and the β1,6-N-acetylglucosamine-containing glycoprotein as a single entity; heating and applying a denaturing agent to the second complex to provide a denatured mixture, in which the β1,6-N-acetylglucosamine-containing glycoprotein may be disassociated from the $L_4$-PHA moiety and the glycan bead; separating the glycan bead from the denatured mixture to provide the β1,6-N-acetylglucosamine-containing glycoprotein substantially free of the glycan bead; subsequently fragmentizing the β1,6-N-acetylglucosamine-containing glycoprotein into smaller fragments; and analyzing the fragments using a mass spectrometric procedure to determine a level of the β1,6-N-acetylglucosamine-containing glycoprotein in the sample.

The foregoing method may further comprise: collecting, from the test mixture, compounds and complexes that comprise a glycan bead while substantially excluding other compounds and complexes that do not contain a glycan bead, wherein the collected compounds and complexes comprise the second complex. The first complex may further comprise a bridge interconnecting the glycan bead and the $L_4$-PHA moiety, wherein the bridge may comprise a ligand receptor and a ligand engaged with the ligand receptor, wherein the ligand may be attached to one of the $L_4$-PHA moiety and the glycan bead, wherein the ligand receptor may be attached to the other of the $L_4$-PHA moiety and the glycan bead. Heating and applying a denaturing agent may cause to disengage the ligand from the ligand receptor, thereby further disassociating the $L_4$-PHA moiety from the glycan bead, whereby the denatured mixture may comprise the β1,6-N-acetylglucosamine-containing glycoprotein, the $L_4$-PHA moiety and the glycan bead as separate entities. Separating may comprise running an electrophoresis in a gel medium, thereby separating the glycan bead from the β1,6-N-acetylglucosamine-containing glycoprotein and the $L_4$-PHA moiety in the denatured mixture. Fragmentizing may comprise contacting an enzymatic agent with the β1,6-N-acetylglucosamine-containing glycoprotein and the $L_4$-PHA moiety.

In the foregoing method, the first complex may further comprise a bridge interconnecting the glycan bead and the $L_4$-PHA moiety, wherein the bridge may comprise a biotin and an avidin engaged with the biotin, wherein the biotin may be attached to one of the $L_4$-PHA moiety and the glycan bead, wherein the avidin may be attached to the other of the $L_4$-PHA moiety and the glycan bead. Separating may comprise running an electrophoresis in a gel medium, thereby separating the glycan bead from the β1,6-N-acetylglucosamine-containing glycoprotein. Fragmentizing may comprise contacting an enzymatic agent with the β1,6-N-acetylglucosamine-containing glycoprotein. The enzymatic agent may be applied to the gel medium containing the β1,6-N-acetylglucosamine-containing glycoprotein. The glycan bead may be selected from the group consisting of an agarose bead and a sepharose bead. The sample may comprise at least one selected from the group consisting of cultured cell lines, cells obtained from a subject, a tissue obtained from a subject, and serum obtained from a subject. The sample may further comprise peptides that are not specific to the binding site, wherein contacting the test agent with the sample provides additional complexes, in which one or more peptides are bound to at least one of the $L_4$-PHA moiety and the glycan bead of the first complex at one or more locations other than the binding site.

Another aspect of the invention provides a diagnostic method for at least one of tumorigenesis and cancer metastasis. The method comprises: the foregoing method of analyzing a sample to determine a level of a β1,6-N-acetylglucosamine-containing glycoprotein; and determining if the level is indicative of at least one of tumorigenesis and cancer metastasis.

A further aspect of the invention provides a kit for determining a level of a β1,6-N-acetylglucosamine-containing glycoprotein in a sample. The kit comprises: a first complex comprising a glycan bead, an phytohemagglutinin-L4 ($L_4$-PHA) moiety and a bridge linking between the glycan bead and the $L_4$-PHA moiety, wherein the $L_4$-PHA moiety may comprise a binding site specific to β1,6-N-acetylglucosamine, wherein the bridge may comprise a ligand and a ligand receptor engaged with the ligand, wherein the ligand is attached to one of the $L_4$-PHA moiety and the glycan bead, wherein the ligand receptor is attached to the other of the $L_4$-PHA moiety and the glycan bead; and wherein the first complex is configured to contact with a sample comprising a β1,6-N-acetylglucosamine-containing glycoprotein such that the first complex binds with the β1,6-N-acetylglucosamine-containing glycoprotein at the binding site to form a second complex, which may comprise the glycan bead, the $L_4$-PHA moiety and the β1,6-N-acetylglucosamine-containing glycoprotein in a single entity.

The foregoing kit may further comprise: a denaturing agent configured for use in disassociating the ligand from the ligand receptor. The ligand may comprise a biotin, and the ligand receptor may comprise an avidin. The glycan bead may be selected from the group consisting of an agarose bead and a sepharose bead. The sample may comprise at least one selected from the group consisting of cultured cell lines, cells obtained from a subject, a tissue obtained from a subject, and serum obtained from a subject.

BRIEF DESCRIPTION OF DRAWINGS

FIG. 1 illustrates the structure of N-linked glycan linkages formed by various glycosyltransferases and L-PHA-binding β1,6-N-acetylglucosamine moiety.

FIG. 2 schematizes the procedures described in Example 1.

FIG. 3 shows the proteins identified according to the method described in Example 1, indicating that many of non-glycoproteins, but not a positive control TIMP-1, were detected.

FIG. 4 schematizes the procedures described in Example 2.

FIG. 5 shows the proteins identified according to the method described in Example 2, indicating that relatively more glycoproteins were detected with low score values and TIMP-1 was not detected still.

FIG. 6 schematizes the procedures described in Example 3.

FIG. 7 is one of the results derived from the method described in Example 3, indicating that many of glycoproteins including TIMP-1 were detected with significant score values.

FIG. 8 shows the proteins that are commonly identified through the method in Example 3 and the previous lectin blot analysis.

FIG. 9 shows the proteins that are identified through the method in Example 3, but not through the previous lectin blot analysis.

FIG. 10 is the comparative result of Example 2 and Example 3, indicating that a mass peak was detected at the retention time of 34.36 min. only through the method of Example 3.

FIG. 11 is a result of the multiple reaction monitoring (MRM) experiment, indicating that a TIMP-1 peptide was detected only in the Example 3.

DETAILED DESCRIPTION OF EMBODIMENTS

The object of the present invention is to provide a sensitive method for identifying glycoproteins acquiring changed glycan structures, termed aberrant glycoproteins, associated with tumorigenesis and cancer metastasis.

Another object of the present invention is to detect and identify aberrant glycoproteins involved in tumorigenesis and cancer metastasis by a simpler method.

For these objects, the inventors have developed the procedure for the detection of aberrant glycoproteins carrying β1,6-N-acetylglucosamine by probing them using L-PHA, a lectin recognizing N-linked glycoproteins with β1,6-N-acetylglucosamine moiety.

The present invention allows to detect even sparse proteins by providing methods in which aberrant glycoproteins carrying β1,6-N-acetylglucosamine involved in tumorigenesis and cancer metastasis are enriched by lectin precipitation. And, the present invention can be applied to every other cancer and to bio-materials including urine and blood.

The present invention provides the analytical method for detecting aberrant glycosylation involved in tumorigenesis and cancer metastasis using lectin precipitation and a list of aberrant glycoproteins as marker candidates for cancer diagnosis.

The present invention is on the sensitive analytical method for identifying glycoproteins carrying an aberrant glycosylation associated with tumorigenesis and cancer metastasis through lectin precipitation.

The applicable cancer type is selected from a group including colon, gastric, lung, liver, cervix, breast, and pancreatic cancer, but is not restricted to the mentioned cancer and can be extended to every cancer type.

The present invention provides a sensitive analytical method for identifying N-linked glycoproteins acquiring β1,6-N-acetylglucosamine moiety from cancer cells. GnT-V that catalyzes the formation of β1,6-N-acetylglucosamine is widely expressed in the various cancer tissues and thus involved the pathology. As β1,6-N-acetylglucosamine is recognized by phytohemagglutinin-L4 (abbreviated as "L4-PHA" or "L-PHA" hereinafter), biotin-labeled L-PHA can be noncovalently conjugated to avidin-agarose beads. The complexes can be, in turn, used to enrich β1,6-N-acetylglucosamine-carrying glycoproteins from protein preparations.

The present invention provides a method for the identification of sparse proteins in which 1,6-N-acetylglucosamine-carrying glycoproteins are trypsinized and subjected to the amino acid sequencing using 7-Teslar Fourier Transform Ion Cyclotron Resonance (FTICR) mass spectrometry.

One aspects of the invention provides a glycoprotein analyzing method containing:

Conjugating ligand-bound L4-PHA with a ligand receptor-attached glycan beads to form L4-PHA-glycan bead complex;

Reacting a sample with the said L4-PHA-glycan bead complex to get glycoproteins;

Running the said glycoproteins by gel electrophoresis;

In-gel digesting the resulted gel containing the said glycoproteins to peptides; and Analyzing the digested peptides by mass spectrometry.

Another aspect of the invention provides the above method, wherein the glycan beads is selected from a group consisting of agarose beads and sepharose beads.

Another aspect of the invention provides the above method, wherein the ligand and the ligand receptor are biotin and avidin.

Another aspect of the invention provides the above method, wherein the sample is native form or denatured form.

Another aspect of the invention provides the above method, wherein the denatured form is generated by at least one selected from a group consisting of β-mercaptoethanol, iodoacetic acid and iodoacetamide.

Another aspect of the invention provides a detection method for glycoproteins that shows a difference in the glycan structure with respect to β1,6-N-acetylglucosamine by respectively adding control and experimental cultured cell lines to L4-PHA-glycan bead complex which is made by conjugating ligand-bound L4-PHA with a ligand receptor-attached glycan beads.

Another aspect of the invention provides a detection method for glycoproteins that shows a difference in the glycan structure with respect to β1,6-N-acetylglucosamine by respectively adding normal sera and experimental sera to L4-PHA-glycan bead complex which is made by conjugating ligand-bound L4-PHA with a ligand receptor-attached glycan beads.

Another aspect of the invention provides an identification method that provides a basis for validation of previously discovered cancer biomarker candidates with a minimal interference by highly abundant serum proteins like albumin, globulin, and transferrin, and can be combined with SIS-CAPA method (Stable Isotope Standards and Capture by Anti-peptide Antibodies: Pearson et al, 2004, J. Proteome Res. 3, 235-44) for maximizing the validation efficiency.

Cancer metastasis arises from dysfunctions in the cell recognition and adhesion, and many of membrane or secreted proteins are involved in the processes, which indicates that biofluids like blood and urine in which a potential biomarker may exist can be used as source of biomarker detection. To find a colon cancer-specific biomarker, The present inventors performed a glycomics study, where GnT-V gene was stably transfected into WiDr, a colon cancer cell line with low expression level of GnT-V. Proteins from the cultured media was resolved on 2-DE gels, which were used for staining with Coomassie Brilliant Blue or lectin blot analysis, and proteins showing differential glycan structures were selected between parental and transfectant WiDr cells (Table 1). However, lectin blot analysis itself has a feasibility of non-specific interaction or implications of contaminant proteins in gels, which requires additional confirmation steps. Moreover, 2-DE gels have a limited resolution capacity and thus sparse proteins are difficult to identify under the gel-based systems. To overcome those limitations, the inventors adopted a method enabling to detect directly β1,6-N-acetyglucosaminylated glycoproteins using a specific lectin.

TABLE 1

| Accession gi NO. | Identities | Peptides matched | Sequence Coverage[a] (%) | Total Score[b] | Mr/pI[c] |
|---|---|---|---|---|---|
| 177836 | α-1-antitrypsin | 8 | 31.1 | 380 | 46.7/5.5 |
| 532198 | Angiotensinogen | 5 | 14.6 | 237 | 53.2/5.8 |
| 123081 | -hexosaminidase chain precursor | 3 | 5.0 | 104 | 63.1/6.3 |
| 4503143 | Cathepsin D preproprotein | 8 | 23.5 | 459 | 44.6/6.1 |
| 3650498 | Cathepsin X precursor | 7 | 28.0 | 291 | 33.9/7.1 |
| 230581 | Chain H, Immunoglobulin G1 | 6 | 17.9 | 314 | 49.7/8.5 |
| 21617867 | Dipeptidyl aminopeptidase II | 4 | 8.9 | 169 | 54.3/5.9 |
| 38327632 | Discoidin receptor tyrosine kinase isoform b | 2 | 3.1 | 96 | 97.2/6.1 |
| 4758116 | Dystroglycan 1 precursor | 2 | 3.0 | 140 | 97.6/8.7 |
| 77416865 | Granulins precursor | 4 | 7.4 | 182 | 63.5/6.4 |
| 5729877 | Heat shock 70 kDa protein 8 isoform 1 | 9 | 17.0 | 278 | 70.9/5.4 |
| 20149594 | Heat shock 90 kDa protein 1, beta | 7 | 11.3 | 229 | 83.3/5.0 |
| 11602963 | Heparan sulfate proteoglycan perlecan | 5 | 2.2 | 175 | 466.6/6.0 |
| 4504371 | Hexosaminidase A preproprotein | 8 | 17.0 | 470 | 60.7/5.0 |
| 106586 | Ig kappa chain V-III | 2 | 10.7 | 124 | 23.1/5.8 |
| 1944352 | IgG Fc binding protein | 5 | 3.2 | 242 | 572.1/5.1 |
| 14583014 | laminin receptor-like protein 5 | 2 | 9.2 | 116 | 33.0/4.8 |
| 2842759 | Legumain precursor | 3 | 10.4 | 110 | 49.4/6.1 |
| 4557747 | Met proto-oncogene precursor | 11 | 9.1 | 512 | 155.5/7.0 |
| 4503899 | N-acetylgalactosamine-6-sulfatase | 5 | 14.9 | 309 | 58.0/6.3 |
| 4504061 | N-acetylglucosamine-6-sulfatase | 9 | 17.2 | 469 | 62.0/8.6 |
| 4505375 | Neogenin homolog 1 | 5 | 4.7 | 248 | 160.0/6.1 |
| 32485152 | Prolyl 4-hydroxylase | 5 | 15.2 | 247 | 84.8/5.3 |
| 11386147 | Prosaposin | 8 | 19.9 | 392 | 58.1/5.1 |
| 4505989 | Protective protein for -galactosidase | 3 | 6.7 | 127 | 54.5/6.2 |
| 729008 | Protein tyrosine kinase 6 | 3 | 5.1 | 76 | 101.1/6.4 |
| 15826840 | Protein tyrosine kinase 7 | 9 | 11.5 | 477 | 118.4/6.7 |
| 5231228 | Ribonuclease T2 precursor | 5 | 22.6 | 247 | 29.5/6.7 |
| 11545839 | Serine protease 22 | 2 | 11.0 | 117 | 33.7/7.6 |
| 135850 | Tissue inhibitor of metalloproteinase-1 | 2 | 7.2 | 102 | 24.2/8.5 |
| 120749 | Tumor-associated calcium signal transducer 1 precursor | 2 | 11.8 | 163 | 34.9/7.4 |
| 4507677 | Tumor rejection antigen-1 (gp96) | 15 | 19.3 | 440 | 92.5/4.8 |
| 38026 | Zn--2-glycoprotein | 10 | 40.4 | 361 | 34.7/5.7 |

[a]Sequence coverage refers to the percentage of peptides that was identified by mass spectrometer.
[b]Total score is a sum of the score values obtained from each of an individual peptide. Score is $-10 \times \mathrm{Log}(P)$, where P is the probability that the observed match is a random event; it is based on NCBInr database using the MASCOT searching program as MS/MS data.
[c]Molecular weight (Mr) and isoelectric point (pI) are theoretical values where glycan residues were not considered for the calculations.

Although L-PHA can bind to β1,6-N-acetylglucosaminylated glycoproteins with a high specificity, it is difficult to detach the bound proteins due to an unavailability of the elution method. To solve the problem, the inventors have the L-PHA-bound proteins run on an SDS-PAGE gel minimally, and the gels were sliced and trypsinized for protein identifications.

Various aspects and embodiments of the present invention will be explained in more detail with reference to the following examples.

Example 1

Enrichment of β1,6-N-Acetylglucosaminylated Glycoproteins Using a Lectin

WiDr:mock cells with a low GnT-V expression level and GnT-V transfectant WiDr:GnT-V were established as model cell lines and conditioned serum-free media were collected from the cell lines. As cancer metastasis has been known to arise from dysfunctions in the cell recognition and adhesion (Egeblad et al., 2002, Nature Rev. 2:161-174; Kannagi et al., 2004, Cancer Sci. 95(5):377-384), and many of membrane or secreted proteins are involved in the processes, β1,6-N-acetylglucosaminylated glycoproteins by GnT-V were purified from the conditioned media. The collected media were concentrated and 1 mg of proteins were allowed to bind to avidin-agarose beads to preclear non-specifically bound proteins. The pre-cleared proteins were allowed to interact with L-PHA-biotin-avidin-agarose beads complexes overnight at 4° C. Though mannose-1,6-N-acetylglucosamine may contribute to detaching the L-PHA bound proteins, the use of the disaccharide is costly and the efficacy has not been demonstrated. Some groups have attempted to detach by acidic elution method but the method has not been demonstrated either and low pH may do damage to the protein integrity. For the reasons, the proteins were digested under the conditions where proteins were bound to the complexes. For this, the protein complexes were washed with excess volumes of PBS buffer and trypsinized with 10 U of trypsin (Promega) overnight at 37° C. The digested peptides were extracted with distilled water and acetonitrile, dried under vacuo and massanalyzed on a 7 Testla FTICR/LTQ mass spectrometer. Proteins were identified from the peptide sequences using Mascot search program (ver. 2.0) (FIGS. 2 & 3).

Database search was done against NCBInr 20051212 (taxonomy; human, entries; 103,913 human sequence entries). As a result, peptides are not effectively sequenced, which are thought to be due to a poor digestion of intact proteins by trypsin. TIMP-1 has previously been identified to be a target for GnT-V and the changed glycan structures were determined by mass spectrometry, which set TIMP-1 as a reference molecule. However, TIMP-1 was not identified in this method and many non-glycoproteins were identified instead.

Example 2

Protein Reduction and Desalting Prior to the Enrichment of β1,6-N-Acetylglucosaminylated Glycoproteins Using a Lectin To reduce a non-specific interaction seen in Example 1 and enhance a sensitivity, proteins from the collected media were reduced by 1% (v/v) β-mercaptoethanol and the unreacted β-mercaptoethanol and salts were removed on a gel-filtration column (FIG. 4). One mg of proteins were precipitated and identified as described in Example 1. The result shows that more glycoproteins were identified, however, with low score value, and TIMP-1 was not identified either.

Example 3

Maximized Protein Digestion in SDS-PAGE Gels and Identification of β1,6-N-Acetylglucosaminylated Glycoproteins Following the Lectin Precipitation Proteins collected from the cultured media as described in Example 1 were reduced by 1% (v/v) β-mercaptoethanol, the unreacted β-mercaptoethanol and salts were removed on a gel-filtration column as described in Example 2. One mg of proteins were precleared with avidin-agarose beads for an hour and the precleared proteins were allowed to bind to L-PHA-biotin-avidin-agarose beads complex overnight at 4° C. After extensive washing with PBS, the bound proteins were separated from the beads complex by adding 1×SDS-PAGE denaturation buffer and boiling briefly. Proteins were resolved on an 8% SDS-PAGE gel and tryptic-digested in gels. The digested peptides were eluted from the gel, resolved using Agilent 1100 Nanoflow systems and sequence-analyzed on a Surveyor system connected to a 7-T FT-LTQ mass spectrometer (Thermo Electron). Peptides were bound and separated on a 10 cm silica column (75 mm) packed with ReproSil-Pur C18-AQ resin (Ammerbuch-Entringen). Peptide mixtures were loaded onto a 100 mm-C18 column (5 μm) by an autosampler (Surveyor) at a flow rate of 20 ml/min. The mobile phases, A and B, were composed of 0% and 100% ACN, respectively, each containing 0.1% formic acid. The gradient began at 5% B for 15 min, was ramped to 20% B for 3 min, to 50% for 47 min, and finally to 95%. The eluted peptides were directly electrosprayed into the mass spectrometer. The mass spectrometer was controlled by Xcalibur software (ThermoElectron Corp., Version 1.4SR1). FIG. 7 represents one of the results. This example allowed to 1) identify glycoproteins with significant score values ($P<0.05$), 2) detect TIMP-1 as in FIG. 7, 3) confirm the proteins that were previously identified through the lectin blot-based identification method (FIG. 8), and 4) detect proteins showing a low expression level with high score values (FIG. 9).

Example 4

Confirmation of the Lectin Precipitation-Based Protein Identification by Mass Spectrometry To compare Example 2 and Example 3, a readily-detected peptide of TIMP-1, GFQALGDAADIR (SEQ ID NO:1), was monitored by mass spectrometry. As shown in FIG. 10, GFQALGDAADIR (SEQ ID NO:1) shows a molecular weight of 1,232 Da and 617.31 m/z in the −2 charge state. A peptide was detected at the retention time of 34 min. in the Example 3, but not in Example 2 and the peptide sequence was found to be GFQALGDAADIR (SEQ ID NO:1). In addition, FIG. 3 shows a parent ion of a peptide detected at m/z 617.31 and a fragment ion at m/z 717.36 in the Example 3, none of which were detected in the Example 2 presumably due to a poor tryptic digestion and extraction. The inventors concluded from those results that Example 3 is an optimized method for identifying 1,6-N-acetylglucosaminylated glycoproteins.

Therefore, the present invention provides far more sensitive method than the 2-DE-based method for identifying sparse proteins showing glycosylation changes.

The present invention enables to diagnose cancer with ease at early stage by differentiating the levels and structures of glycoproteins between normal and experimental samples.

What is claimed is:

1. A method of analyzing a sample to determine a level of a β1,6-N-acetylglucosamine-containing glycoprotein, the method comprising:

providing a test agent comprising a first complex, wherein the first complex comprises a glycan bead and an phytohemagglutinin-L4 ($L_4$-PHA) moiety connected to the glycan bead, wherein the $L_4$-PHA moiety comprises a binding site specific to β1,6-N-acetylglucosamine;

providing a sample comprising a β1,6-N-acetylglucosamine-containing glycoprotein;

contacting the test agent with the sample to provide a test mixture, in which the β1,6-N-acetylglucosamine-containing glycoprotein binds with the first complex at the binding site, thereby forming a second complex in the mixture, wherein the second complex comprises the glycan bead, the $L_4$-PHA moiety and the β1,6-N-acetylglucosamine-containing glycoprotein as a single entity;

heating and applying a denaturing agent to the second complex to provide a denatured mixture, in which the β1,6-N-acetylglucosamine-containing glycoprotein is disassociated from the $L_4$-PHA moiety and the glycan bead;

separating the glycan bead from the denatured mixture to provide the β1,6-N-acetylglucosamine-containing glycoprotein substantially free of the glycan bead;

subsequently fragmentizing the β1,6-N-acetylglucosamine-containing glycoprotein into smaller fragments; and analyzing the fragments using a mass spectrometric procedure to determine a level of the β1,6-N-acetylglucosamine-containing glycoprotein in the sample.

2. The method of claim 1, further comprising:
collecting, from the test mixture, compounds and complexes that comprise a glycan bead while substantially excluding other compounds and complexes that do not contain a glycan bead, wherein the collected compounds and complexes comprise the second complex.

3. The method of claim 1, wherein the first complex further comprises a bridge interconnecting the glycan bead and the $L_4$-PHA moiety, wherein the bridge comprises a ligand receptor and a ligand engaged with the ligand receptor, wherein the ligand is attached to the $L_4$-PHA moiety, wherein the ligand receptor is attached to the glycan bead.

4. The method of claim 3, wherein heating and applying a denaturing agent causes to disengage the ligand from the ligand receptor, thereby further disassociating the $L_4$-PHA moiety from the glycan bead, whereby the denatured mixture comprises the β1,6-N-acetylglucosamine-containing glycoprotein, the $L_4$-PHA moiety and the glycan bead as separate entities.

5. The method of claim 4, wherein separating comprises running an electrophoresis in a gel medium, thereby separating the glycan bead from the β1,6-N-acetylglucosamine-containing glycoprotein and the $L_4$-PHA moiety in the denatured mixture.

6. The method of claim 5, wherein fragmentizing comprises contacting an enzymatic agent with the β1,6-N-acetylglucosamine-containing glycoprotein and the $L_4$-PHA moiety.

7. The method of claim 1, wherein the first complex further comprises a bridge interconnecting the glycan bead and the $L_4$-PHA moiety, wherein the bridge comprises a biotin and an avidin engaged with the biotin, wherein the biotin is attached to the $L_4$-PHA moiety, wherein the avidin is attached to the glycan bead.

8. The method of claim 1, wherein separating comprises running an electrophoresis in a gel medium, thereby separating the glycan bead from the β1,6-N-acetylglucosamine-containing glycoprotein.

9. The method of claim 1, wherein fragmentizing comprises contacting an enzymatic agent with the β1,6-N-acetylglucosamine-containing glycoprotein.

10. The method of claim 9, wherein the enzymatic agent is applied to the gel medium containing the β1,6-N-acetylglucosamine-containing glycoprotein.

11. The method of claim 1, wherein the glycan bead is selected from the group consisting of an agarose bead and a sepharose bead.

12. The method of claim 1, wherein the sample comprises at least one selected from the group consisting of cultured cell lines, cells obtained from a subject, a tissue obtained from a subject, and serum obtained from a subject.

13. The method of claim 1, wherein the sample further comprises peptides that are not specific to the binding site, wherein contacting the test agent with the sample provides additional complexes, in which one or more peptides are bound to at least one of the $L_4$-PHA moiety and the glycan bead of the first complex at one or more locations other than the binding site.

14. The method of claim 1, wherein the first complex further comprises a bridge interconnecting the glycan bead and the $L_4$-PHA moiety, wherein the bridge comprises a ligand receptor and a ligand engaged with the ligand receptor, wherein the ligand is attached to the glycan bead, wherein the ligand receptor is attached to the $L_4$-PHA moiety.

15. The method of claim 1, wherein the first complex further comprises a bridge interconnecting the glycan bead and the $L_4$-PHA moiety, wherein the bridge comprises a biotin and an avidin engaged with the biotin, wherein the biotin is attached to the glycan bead, wherein the avidin is attached to the $L_4$-PHA moiety.

* * * * *

SEQUENCE LISTING

```
<160> NUMBER OF SEQ ID NOS: 26

<210> SEQ ID NO 1
<211> LENGTH: 12
<212> TYPE: PRT
<213> ORGANISM: Homo sapiens

<400> SEQUENCE: 1

Gly Phe Gln Ala Leu Gly Asp Ala Ala Asp Ile Arg
1               5                   10

<210> SEQ ID NO 2
<211> LENGTH: 12
<212> TYPE: PRT
<213> ORGANISM: Homo sapiens

<400> SEQUENCE: 2
```

```
Arg Ala His Val Glu Gly Pro Ser Cys Asp Arg Cys
1               5                   10

<210> SEQ ID NO 3
<211> LENGTH: 11
<212> TYPE: PRT
<213> ORGANISM: Homo sapiens

<400> SEQUENCE: 3

Arg Trp Trp Gln Ser Pro Pro Leu Ser Arg Gly
1               5                   10

<210> SEQ ID NO 4
<211> LENGTH: 14
<212> TYPE: PRT
<213> ORGANISM: Homo sapiens

<400> SEQUENCE: 4

Arg Tyr Val Asn Arg Gly Ala Met Ser Val Ser Gly Arg Val
1               5                   10

<210> SEQ ID NO 5
<211> LENGTH: 13
<212> TYPE: PRT
<213> ORGANISM: Homo sapiens

<400> SEQUENCE: 5

Arg Asp His Tyr Leu Pro Asp Leu His His Leu Arg Leu
1               5                   10

<210> SEQ ID NO 6
<211> LENGTH: 17
<212> TYPE: PRT
<213> ORGANISM: Homo sapiens

<400> SEQUENCE: 6

Arg Leu Glu Leu Glu Ala Ala Thr Pro Glu Gly His Ala Met Arg
1               5                   10                  15

Phe

<210> SEQ ID NO 7
<211> LENGTH: 21
<212> TYPE: PRT
<213> ORGANISM: Homo sapiens

<400> SEQUENCE: 7

Lys Arg Leu Asn Thr Thr Gly Val Ser Ala Gly Cys Thr Ala Asp Leu
1               5                   10                  15

Leu Val Gly Arg Ala
            20

<210> SEQ ID NO 8
<211> LENGTH: 23
<212> TYPE: PRT
<213> ORGANISM: Homo sapiens

<400> SEQUENCE: 8

Lys Cys Asp Gln Cys Ser Leu Gly Thr Phe Ser Leu Asp Ala Ala Asn
1               5                   10                  15

Pro Lys Gly Cys Thr Arg Cys
            20

<210> SEQ ID NO 9
```

```
<211> LENGTH: 23
<212> TYPE: PRT
<213> ORGANISM: Homo sapiens

<400> SEQUENCE: 9

Arg Cys Asp Cys Thr Pro Cys Gly Thr Glu Ala Cys Asp Pro His Ser
1               5                   10                  15

Gly His Cys Leu Cys Lys Ala
            20

<210> SEQ ID NO 10
<211> LENGTH: 27
<212> TYPE: PRT
<213> ORGANISM: Homo sapiens

<400> SEQUENCE: 10

Arg Glu Gln Val Leu Pro Ala Gly Gln Ile Val Asn Cys Asp Cys Ser
1               5                   10                  15

Ala Ala Gly Thr Gln Gly Asn Ala Cys Arg Lys
            20                  25

<210> SEQ ID NO 11
<211> LENGTH: 26
<212> TYPE: PRT
<213> ORGANISM: Homo sapiens

<400> SEQUENCE: 11

Arg Cys Lys Pro Gly Phe Trp Gly Leu Ser Pro Ser Asn Pro Glu Gly
1               5                   10                  15

Cys Thr Arg Cys Ser Cys Asp Leu Arg Gly
            20                  25

<210> SEQ ID NO 12
<211> LENGTH: 27
<212> TYPE: PRT
<213> ORGANISM: Homo sapiens

<400> SEQUENCE: 12

Arg Ala Asp Asp Gly Ala Gly Glu Phe Ser Thr Ser Val Thr Arg Pro
1               5                   10                  15

Ser Val Leu Cys Asp Gly Gln Trp His Arg Leu
            20                  25

<210> SEQ ID NO 13
<211> LENGTH: 28
<212> TYPE: PRT
<213> ORGANISM: Homo sapiens

<400> SEQUENCE: 13

Arg Glu Gln Val Leu Pro Ala Gly Gln Ile Val Asn Cys Asp Cys Ser
1               5                   10                  15

Ala Ala Gly Thr Gln Gly Asn Ala Cys Arg Lys Asp
            20                  25

<210> SEQ ID NO 14
<211> LENGTH: 33
<212> TYPE: PRT
<213> ORGANISM: Homo sapiens

<400> SEQUENCE: 14

Arg Gly Thr Leu Gly Gly Val Ala Glu Cys Gln Pro Gly Thr Gly Gln
1               5                   10                  15

Cys Phe Cys Lys Pro His Val Cys Gly Gln Ala Cys Ala Ser Cys Lys
```

```
                  20                  25                  30
Asp

<210> SEQ ID NO 15
<211> LENGTH: 13
<212> TYPE: PRT
<213> ORGANISM: Homo sapiens

<400> SEQUENCE: 15

Arg Ala Leu Asp Phe Ala Val Gly Glu Tyr Asn Lys Ala
1               5                   10

<210> SEQ ID NO 16
<211> LENGTH: 19
<212> TYPE: PRT
<213> ORGANISM: Homo sapiens

<400> SEQUENCE: 16

Arg Leu Val Gly Gly Pro Met Asp Ala Ser Val Glu Glu Glu Gly Val
1               5                   10                  15

Arg Arg Ala

<210> SEQ ID NO 17
<211> LENGTH: 8
<212> TYPE: PRT
<213> ORGANISM: Homo sapiens

<400> SEQUENCE: 17

Arg Val Glu Ile Phe Tyr Arg Gly
1               5

<210> SEQ ID NO 18
<211> LENGTH: 11
<212> TYPE: PRT
<213> ORGANISM: Homo sapiens

<400> SEQUENCE: 18

Arg Ile Asp Ile Thr Leu Ser Ser Val Lys Cys
1               5                   10

<210> SEQ ID NO 19
<211> LENGTH: 14
<212> TYPE: PRT
<213> ORGANISM: Homo sapiens

<400> SEQUENCE: 19

Arg Ala Ser His Glu Glu Val Glu Gly Leu Val Glu Lys Ile
1               5                   10

<210> SEQ ID NO 20
<211> LENGTH: 15
<212> TYPE: PRT
<213> ORGANISM: Homo sapiens

<400> SEQUENCE: 20

Arg Ser Asp Leu Ala Val Pro Ser Glu Leu Ala Leu Leu Lys Ala
1               5                   10                  15

<210> SEQ ID NO 21
<211> LENGTH: 16
<212> TYPE: PRT
<213> ORGANISM: Homo sapiens

<400> SEQUENCE: 21
```

-continued

```
Arg Glu Leu Ser Glu Ala Leu Gly Gln Ile Phe Asp Ser Gln Arg Gly
1               5                   10                  15

<210> SEQ ID NO 22
<211> LENGTH: 21
<212> TYPE: PRT
<213> ORGANISM: Homo sapiens

<400> SEQUENCE: 22

Arg Ile Tyr Thr Ser Pro Thr Trp Ser Ala Phe Val Thr Asp Ser Ser
1               5                   10                  15

Trp Ser Ala Arg Lys
            20

<210> SEQ ID NO 23
<211> LENGTH: 22
<212> TYPE: PRT
<213> ORGANISM: Homo sapiens

<400> SEQUENCE: 23

Arg Tyr Tyr Pro Tyr Gln Ser Phe Gln Thr Pro Gln His Pro Ser Phe
1               5                   10                  15

Leu Phe Gln Asp Lys Arg
            20

<210> SEQ ID NO 24
<211> LENGTH: 30
<212> TYPE: PRT
<213> ORGANISM: Homo sapiens

<400> SEQUENCE: 24

Arg Ala Ala Phe Gly Gln Gly Ser Gly Pro Ile Met Leu Asp Glu Val
1               5                   10                  15

Gln Cys Thr Gly Thr Glu Ala Ser Leu Ala Asp Cys Lys Ser
            20                  25                  30

<210> SEQ ID NO 25
<211> LENGTH: 11
<212> TYPE: PRT
<213> ORGANISM: Homo sapiens

<400> SEQUENCE: 25

Arg Ser Glu Glu Phe Leu Ile Ala Gly Lys Leu
1               5                   10

<210> SEQ ID NO 26
<211> LENGTH: 14
<212> TYPE: PRT
<213> ORGANISM: Homo sapiens

<400> SEQUENCE: 26

Lys Gly Phe Gln Ala Lys Gly Asp Ala Ala Asp Ile Arg Phe
1               5                   10
```